(12) United States Patent
Karo

(10) Patent No.: US 8,777,864 B2
(45) Date of Patent: Jul. 15, 2014

(54) CUFF FOR BLOOD PRESSURE MONITOR AND BLOOD PRESSURE MONITOR HAVING THE SAME

(75) Inventor: Hiromichi Karo, Kyoto (JP)

(73) Assignee: Omron Healthcare Co., Ltd., Kyoto-shi (JP)

(*) Notice: Subject to any disclaimer, the term of this patent is extended or adjusted under 35 U.S.C. 154(b) by 1049 days.

(21) Appl. No.: 12/158,562

(22) PCT Filed: Nov. 10, 2006

(86) PCT No.: PCT/JP2006/322451
§ 371 (c)(1),
(2), (4) Date: Jun. 20, 2008

(87) PCT Pub. No.: WO2007/074589
PCT Pub. Date: Jul. 5, 2007

(65) Prior Publication Data
US 2009/0234381 A1    Sep. 17, 2009

(30) Foreign Application Priority Data
Dec. 27, 2005 (JP) .................................. 2005-375425

(51) Int. Cl.
*A61B 5/02* (2006.01)
(52) U.S. Cl.
USPC ....................................................... 600/490
(58) Field of Classification Search
USPC .......................................... 600/485, 490–499
See application file for complete search history.

(56) References Cited
U.S. PATENT DOCUMENTS

| 3,120,846 A |   | 2/1964 | Fletcher |         |
|-------------|---|--------|----------|---------|
| 5,511,552 A | * | 4/1996 | Johnson  | 600/499 |

(Continued)

FOREIGN PATENT DOCUMENTS

| JP | 55-087204 | 6/1980 |
| JP | 1-112804  | 7/1989 |

(Continued)

OTHER PUBLICATIONS

Japanese Decision to Grant Patent mailed Dec. 14, 2010, directed to counterpart Japanese Patent Application No. 2005-375425; 6 pages.

(Continued)

*Primary Examiner* — Patricia Mallari
*Assistant Examiner* — Vasuda Ramachandran
(74) *Attorney, Agent, or Firm* — Morrison & Foerster LLP

(57) ABSTRACT

A cuff for a blood pressure monitor includes a bag-shaped cover body containing an air bag and a curled elastic member as a curved elastic plate. The bag-shaped cover body is formed by stacking an inner cover member located on a living body side when applied and an outer cover member located on a side opposite to the living body side when applied, one on the other, and sewing their rims. The curled elastic member contained in the bag-shaped cover body includes a large curvature region and a small curvature region in a winding direction thereof to fit a measurement site. In a state where the air bag is not inflated, the inner cover member at a portion corresponding to the large curvature region of the curled elastic member is stretched in a width direction thereof. With this configuration, a cuff for a blood pressure monitor which is less likely to have wrinkles in a bag-shaped cover body can be provided.

11 Claims, 12 Drawing Sheets

(56) References Cited

U.S. PATENT DOCUMENTS

| | | | |
|---|---|---|---|
| 5,743,857 A * | 4/1998 | Shinoda et al. | 600/496 |
| 6,336,901 B1 * | 1/2002 | Itonaga et al. | 600/499 |
| 6,379,310 B1 | 4/2002 | Mori et al. | |
| 6,514,212 B1 | 2/2003 | Ide et al. | |
| 6,645,157 B2 * | 11/2003 | Inagaki | 600/499 |
| 2002/0099299 A1 | 7/2002 | Inagaki | |
| 2003/0171683 A1 | 9/2003 | Inagaki et al. | |
| 2009/0234381 A1 | 9/2009 | Karo | |

FOREIGN PATENT DOCUMENTS

| | | |
|---|---|---|
| JP | 3-82440 | 4/1991 |
| JP | 09-117418 | 5/1997 |
| JP | 9-117419 | 5/1997 |
| JP | 9-238910 | 9/1997 |
| JP | 3164114 | 5/2001 |
| JP | 2002-209858 | 7/2002 |
| RU | 2150300 | 6/2000 |
| RU | 2004136069 | 5/2006 |
| WO | WO-2007/074589 | 7/2007 |

OTHER PUBLICATIONS

Russian Decision on Grant mailed Oct. 6, 2009, directed at counterpart Russian Application No. 2008130886/14(038341); 12 pages.

European Search Report dated Aug. 19, 2011, directed to European Application No. 06 83 2503; 6 pages.

International Search Report Mailed on Nov. 28, 2006 directed to International Application No. PCT/JP2006/322451; 1 page.

\* cited by examiner

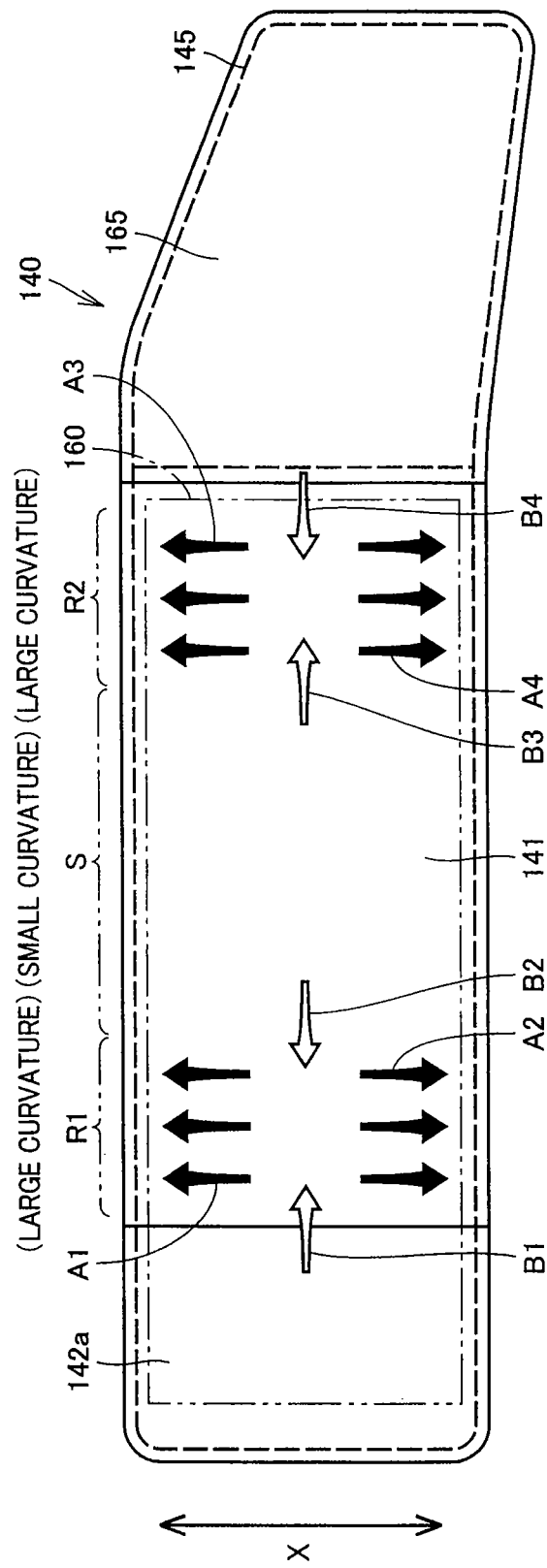

CUFF FOR BLOOD PRESSURE MONITOR AND BLOOD PRESSURE MONITOR HAVING THE SAME

CROSS REFERENCE TO RELATED APPLICATION

This application is a national stage application under 35 USC 371 of International Application No. PCT/JP2006/322451, filed Nov. 10, 2006, which claims the benefit of Japanese Patent Application No. 2005-375425, filed Dec. 27, 2005, the entire contents of these applications being hereby incorporated by reference.

TECHNICAL FIELD

The present invention relates to a cuff for a blood pressure monitor wound around a measurement site of a living body such as a wrist or an upper arm at the time of measurement of blood pressure, and a blood pressure monitor having the cuff.

BACKGROUND ART

Normally, to measure a blood pressure value, a cuff provided with a fluid bag for pressing an artery located within a living body is wound around the body surface, and arterial pressure pulse waves caused in the artery by inflation/deflation of the fluid bag are detected to measure the blood pressure value. Here, the cuff refers to a band-shaped structure having a bladder, which can be wound around a part of a living body, for use in measurement of arterial pressure of an upper limb, a lower limb or the like by introducing fluid such as gas or liquid into the bladder. Thus, the cuff represents the concept including the fluid bag as well as members for winding the fluid bag around the living body. Particularly, the cuff wound around and applied to a wrist or an upper arm is also called an arm band or a manchette.

The cuff for a blood pressure monitor has a bag-shaped cover body containing an air bag as a fluid bag therein. The bag-shaped cover body is usually formed into a bag shape by stacking two sheet-shaped members constituting an inner cover member and an outer cover member one on the other and connecting their rims. The cuff for a blood pressure monitor having such a configuration is disclosed, e.g., in Japanese Patent Laying-Open Nos. 09-117419 (Patent Document 1) and 09-238910 (Patent Document 2).

In recent years, it is common to provide the cuff for a blood pressure monitor with a curled elastic member, identified as an elastic member, within the bag-shaped cover body and on the outer side of the air bag, so as to facilitate the operation of applying the cuff by the subject and also to allow the air bag to expand smoothly toward the living body at the time of pressurizing the air bag after application of the cuff (see, e.g., Patent Documents 1 and 2 described above and Japanese Patent Laying-Open No. 2002-209858 (Patent Document 3)). As the curled elastic member, a plate-like member made of resin, which is wound annularly and elastically deformable in a radial direction, may be used.

Patent Document 1: Japanese Patent Laying-Open No. 09-117419

Patent Document 2: Japanese Patent Laying-Open No. 09-238910

Patent Document 3: Japanese Patent Laying-Open No. 2002-209858

DISCLOSURE OF THE INVENTION

Problems to be Solved by the Invention

Generally, a cuff for a blood pressure monitor having a bag-shaped cover body and a curled elastic member as described above is fabricated by stacking a substantially rectangular-shaped inner cover member and a substantially rectangular-shaped outer cover member having a contour that substantially matches that of the inner cover member one on the other, connecting their end rims along and in parallel with the edges of the inner cover member and the outer cover member to form a bag-shaped cover body, and thereafter inserting a curled elastic member and an air bag into the bag-shaped cover body. Therefore, a space formed within the bag-shaped cover body has a shape in a width direction that is uniform in a longitudinal direction of the bag-shaped cover body.

However, the cuff for a blood pressure monitor fabricated through the process as described above has a problem that the inner cover member is likely to have wrinkles when the cuff is applied to a measurement site. The wrinkles occur because the inner cover member is formed of a material with elasticity higher than that of the outer cover member to avoid obstructing inflation of the air bag, and is configured to be wound annularly to be wound around a living body. In particular, in a cuff for a blood pressure monitor in which a curled elastic member is provided with a large curvature region and a small curvature region to fit the living body, wrinkles occur intensively in the inner cover member at a portion corresponding to the large curvature region of the curled elastic member.

FIG. 13 is a perspective view of a conventional ordinary wrist blood pressure monitor, and FIG. 14 is a cross sectional view showing a state where a cuff for the wrist blood pressure monitor shown in FIG. 13 is wound on a wrist. For example, as shown in FIGS. 13 and 14, in an ordinary wrist blood pressure monitor 100B, a curled elastic member 160 is formed to include a large curvature region and a small curvature region in a winding direction thereof to cause a cuff 130 for the blood pressure monitor to fit a wrist 1 with a flattened shape. Thereby, cuff 130 for the blood pressure monitor also includes a large curvature region and a small curvature region in a winding direction thereof.

Specifically, in a state where cuff 130 for the blood pressure monitor is applied to wrist 1, the curvature of cuff 130 for the blood pressure monitor at a portion to be placed along both side portions of wrist 1 (i.e., a surface portion of wrist 1 at a position corresponding to a portion of a radius 2 on a side opposite to an ulna 3 side and a surface portion of wrist 1 at a position corresponding to a portion of ulna 3 on a side opposite to a radius 2 side) is larger than the curvature of cuff 130 for the blood pressure monitor at a portion to be placed along a portion of wrist 1 other than the both side portions (i.e., a surface portion of wrist 1 at a position corresponding to a portion that continues to the palm side of wrist 1 and a surface portion of wrist 1 at a position corresponding to a portion that continues to the back-of-the-hand side of wrist 1). Therefore, as shown in FIGS. 13 and 14, wrinkles W occur intensively in an inner cover member 141 at a position corresponding to the large curvature portion.

When wrinkles W occur in inner cover member 141, as shown in FIG. 14, an air bag 150 cannot be fully inflated at a portion adjacent to the wrinkles. As a result, compressive force applied to arteries 4 and 5 becomes nonuniform, causing an adverse effect that the accuracy of measuring a blood pressure value is reduced.

In particular, in cuff 130 for the blood pressure monitor in which curled elastic member 160 is provided with a large curvature region and a small curvature region to fit a living body as described above, wrinkles W occur intensively in inner cover member 141 at a portion corresponding to the large curvature region of curled elastic member 160, and compressive force shortage may occur at this portion.

Consequently, the present invention has been made to solve the aforementioned problems, and one object of the present invention is to be able to provide a blood pressure monitor capable of measuring a blood pressure value with high accuracy by implementing a cuff for the blood pressure monitor which is less likely to have wrinkles in a bag-shaped cover body.

Means for Solving the Problems

A cuff for a blood pressure monitor according to the present invention includes: a fluid bag inflated and deflated as a fluid comes in and out; an elastic member located on an outer side of the fluid bag when the fluid bag is wound around a living body, and wound annularly and elastically deformable in a radial direction; and a bag-shaped cover body containing the fluid bag and the elastic member therein and applied to the living body such that a width direction thereof is substantially parallel to an axial direction of the living body. The bag-shaped cover body includes an inner wall portion located on a living body side when the bag-shaped cover body is wound around the living body, and an outer wall portion located on a side opposite to the living body side when where the bag-shaped cover body is wound around the living body. The elastic member includes a large curvature region and a small curvature region in a winding direction thereof to cause the cuff for a blood pressure monitor to fit the living body. In the cuff for a blood pressure monitor, in a state where the fluid bag is deflated, the inner wall portion at a portion corresponding to the large curvature region of the elastic member is stretched in the width direction.

With this configuration, a slack enough to cause occurrence of wrinkles is not formed in the inner wall portion of the bag-shaped cover body at the portion corresponding to the large curvature region of the elastic member, preventing occurrence of wrinkles in this portion. Therefore, a cuff for a blood pressure monitor exerting compressive force uniform over an entire area to an artery when the fluid bag is inflated can be provided. Further, with the configuration described above, the inner wall portion of the bag-shaped cover body at a portion corresponding to the small curvature region of the elastic member is stretched in a longitudinal direction orthogonal to the width direction, simultaneously preventing occurrence of wrinkles in this portion. Therefore, a cuff for a blood pressure monitor exerting compressive force uniform over an entire area to an artery when the fluid bag is inflated can be provided.

In the cuff for a blood pressure monitor according to the present invention, in the state where the fluid bag is deflated, the inner wall portion at a portion corresponding to the small curvature region of the elastic member may be slackened in the width direction. Further, in the cuff for a blood pressure monitor according to the present invention, in the state where the fluid bag is deflated, the inner wall portion at the portion corresponding to the large curvature region of the elastic member may be more stretched in the width direction than the inner wall portion at a portion corresponding to the small curvature region of the elastic member.

As described above, the inner wall portion of the bag-shaped cover body at the portion corresponding to the small curvature region of the elastic member may be slackened in the width direction unlike the inner wall portion of the bag-shaped cover body at the portion corresponding to the large curvature region of the elastic member, or may be stretched in the width direction as with the inner wall portion of the bag-shaped cover body at the portion corresponding to the large curvature region of the elastic member. When the inner wall portion of the bag-shaped cover body at the portion corresponding to the small curvature region of the elastic member is slackened in the width direction, the fluid bag and the elastic member can be easily inserted into the bag-shaped cover body, facilitating fabrication of the cuff for a blood pressure monitor. On the other hand, when the inner wall portion of the bag-shaped cover body at the portion corresponding to the small curvature region of the elastic member is stretched in the width direction, a slack enough to cause occurrence of wrinkles is also not formed in this portion, and thus a cuff for a blood pressure monitor exerting compressive force more uniform over an entire area to an artery when the fluid bag is inflated can be provided.

However, since the inner wall portion of the bag-shaped cover body at the portion corresponding to the small curvature region of the elastic member is inherently less likely to have wrinkles, when compared to the inner wall portion of the bag-shaped cover body at the portion corresponding to the large curvature region of the elastic member, a stretching force in the width direction applied to the inner wall portion of the bag-shaped cover body at the portion corresponding to the small curvature region of the elastic member may be smaller than a stretching force in the width direction applied to the inner wall portion of the bag-shaped cover body at the portion corresponding to the large curvature region of the elastic member. Further, if the inner wall portion is stretched over an entire area of the cuff for a blood pressure monitor, inflation of the fluid bag at the time of measurement may be obstructed. Also from this standpoint, it is preferable to set the stretching force in the width direction applied to the inner wall portion of the bag-shaped cover body at the portion corresponding to the small curvature region of the elastic member to be small.

Preferably, in the cuff for a blood pressure monitor according to the present invention, the inner wall portion is more elastic than the outer wall portion.

With this configuration, inflation of the fluid bag toward the living body is not obstructed by the inner wall portion of the bag-shaped cover body, and thus a cuff for a blood pressure monitor exerting compressive force more uniform over an entire area to an artery when the fluid bag is inflated can be provided.

The cuff for a blood pressure monitor according to the present invention may be configured such that, when the bag-shaped cover body is formed into a bag shape by stacking an inner cover member forming the inner wall portion and an outer cover member forming the outer wall portion one on the other and connecting their rims, the inner cover member at a portion corresponding to the large curvature region of the elastic member is stretched in the width direction in a state after the fluid bag and the elastic member are inserted into the bag-shaped cover body and where the fluid bag is deflated, by forming a connection interval in the width direction with which the inner cover member and the outer cover member are connected at a portion corresponding to the large curvature region of the elastic member to be smaller than a connection interval in the width direction with which the inner cover member and the outer cover member are connected at a portion corresponding to the small curvature region of the elastic member, and, in a state before the fluid bag and the elastic member are inserted into the bag-shaped cover body, forming the connection interval in the width direction with which the inner cover member and the outer cover member are connected at the portion corresponding to the large curvature region of the elastic member to be smaller than a width of the elastic member.

Further, the cuff for a blood pressure monitor according to the present invention may be configured such that, when the bag-shaped cover body is formed into a bag shape by stacking an inner cover member forming the inner wall portion and an outer cover member forming the outer wall portion one on the other and connecting their rims, the inner cover member at a portion corresponding to the large curvature region of the elastic member is stretched in the width direction in the state where the fluid bag is deflated, by placing the inner cover member at the portion corresponding to the large curvature region of the elastic member in a stretched state and connecting the inner cover member to the outer cover member with this state maintained.

Further, the cuff for a blood pressure monitor according to the present invention may be configured such that, when the bag-shaped cover body is formed into a bag shape by stacking an inner cover member forming the inner wall portion and an outer cover member forming the outer wall portion one on the other and connecting their rims, the inner cover member at a portion corresponding to the large curvature region of the elastic member is stretched in the width direction in a state after the fluid bag and the elastic member are inserted into the bag-shaped cover body and where the fluid bag is deflated, by forming a width of the elastic member at the large curvature region of the elastic member to be greater than a width of the elastic member at the small curvature region of the elastic member, and, in a state before the fluid bag and the elastic member are inserted into the bag-shaped cover body, forming a connection interval in the width direction with which the inner cover member and the outer cover member are connected at a portion corresponding to the large curvature region of the elastic member to be smaller than the width of the elastic member at the large curvature region of the elastic member.

By employing any of the configurations described above, a state where the inner wall portion at the portion corresponding to the large curvature region of the elastic member is stretched in the width direction in the state where the fluid bag is deflated can be achieved extremely easily, and thus a cuff for a blood pressure monitor exerting compressive force uniform over an entire area to an artery can be provided at an inexpensive cost.

Preferably, in the cuff for a blood pressure monitor according to the present invention, the inner cover member and the outer cover member are connected by sewing, and/or melting and bonding.

With this configuration, the bag-shaped cover body can be fabricated easily.

A blood pressure monitor according to the present invention includes: any of the cuffs for a blood pressure monitor described above; an inflating/deflating mechanism inflating and deflating the fluid bag; a pressure detecting portion detecting a pressure within the fluid bag; and a blood pressure value calculating portion calculating a blood pressure value based on pressure information detected by the pressure detecting portion.

With this configuration, wrinkles are less likely to occur in the inner wall portion of the bag-shaped cover body, and thus a cuff for a blood pressure monitor exerting compressive force uniform over an entire area to an artery when the fluid bag is inflated can be provided. Therefore, highly accurate blood pressure measurement can be performed by providing a blood pressure monitor having such a cuff.

Effects of the Invention

According to the present invention, a cuff for a blood pressure monitor which is less likely to have wrinkles in a bag-shaped cover body can be provided, and thus a blood pressure value can be measured with high accuracy.

BRIEF DESCRIPTION OF THE DRAWINGS

FIG. 8A is a view showing the state where the inner cover member of the cuff for a blood pressure monitor according to the embodiment of the present invention is stretched, which is a schematic development view of the cuff for a blood pressure monitor when it is developed and seen from a surface to be applied to a living body.

DESCRIPTION OF THE REFERENCE SIGNS

1: wrist, 2: radius, 3: ulna, 4, 5: artery, 100A, 100B: blood pressure monitor, 110: main body, 111: display portion, 112: manipulation portion, 114: memory portion, 115: power supply portion, 120: tube, 121: air system component for blood pressure measurement, 122: pressure sensor, 123: pump, 124: valve, 125: oscillation circuit, 126: pump driving circuit, 127: valve driving circuit, 130: cuff for a blood pressure monitor, 140, 140A-140D: bag-shaped cover body, 141: inner cover member, 142: outer cover member, 142a: folded portion, 145: sewn portion, 146: recessed portion, 147: bonded portion, 150: air bag, 151: inner resin sheet, 152: outer resin sheet, 154: inflated/deflated space, 160: curled elastic member, 161a, 161b: engagement hook portion, 162: hole, 164: projecting portion, 165, 166: loop and hook fasteners.

BEST MODES FOR CARRYING OUT THE INVENTION

Hereinafter, an embodiment of the present invention will be described in detail with reference to the drawings. In the following embodiment, a wrist blood pressure monitor will be described as an example of the blood pressure monitor.

Figure 1:
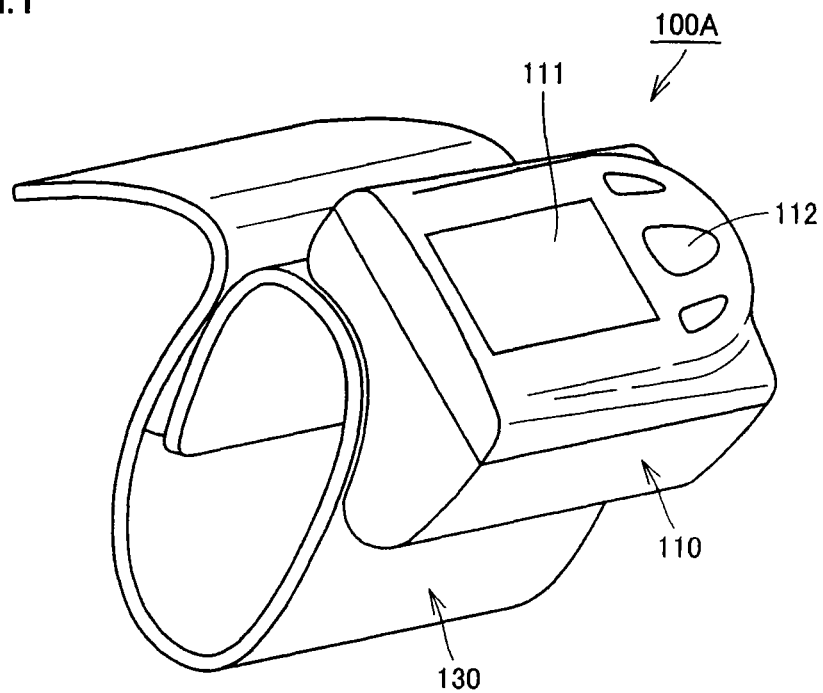
FIG. 1 is a perspective view showing an appearance of a blood pressure monitor according to an embodiment of the present invention.

FIG. 1 is a perspective view showing an appearance of a blood pressure monitor according to the embodiment of the present invention. As shown in FIG. 1, a blood pressure monitor 100A of the present embodiment includes a main body 110 and a cuff 130. A display portion 111 and a manipulation portion 112 are arranged on a surface of main body 110. Cuff 130 is attached to main body 110.

Figure 2:
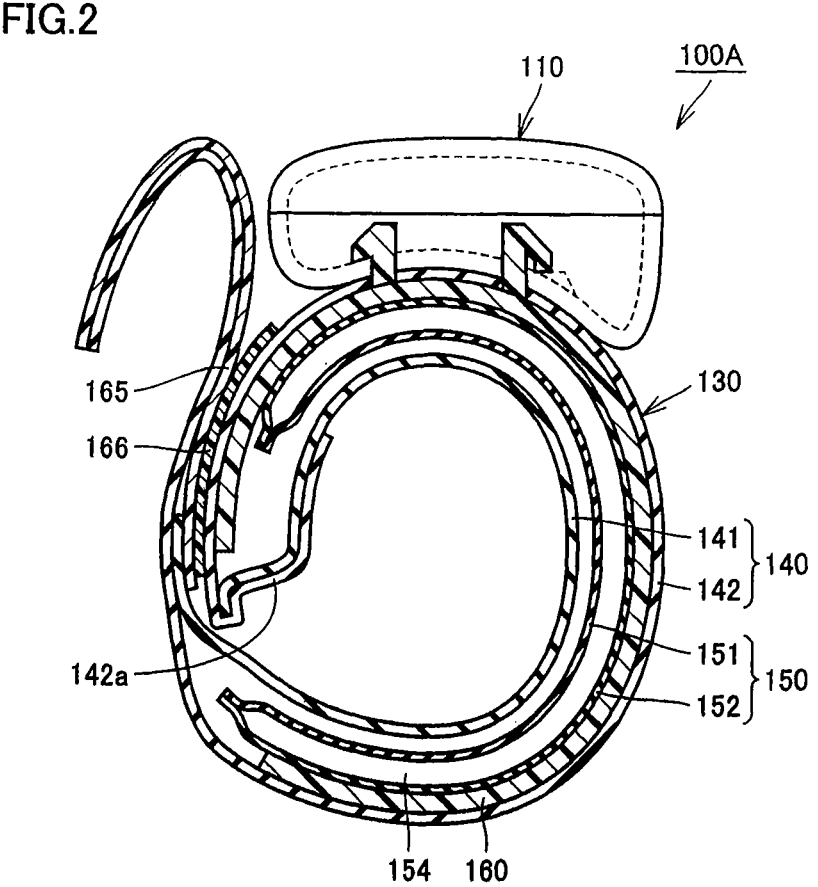
FIG. 2 is a vertical cross sectional view showing an inner structure of the blood pressure monitor according to the embodiment of the present invention.

FIG. 2 is a vertical cross sectional view showing an inner structure of the blood pressure monitor of the present embodiment. As shown in FIG. 2, cuff 130 for the blood pressure monitor of the present embodiment primarily includes a bag-shaped cover body 140 that is made of cloth or the like, an air bag 150 identified as a fluid bag that is arranged inside bag-shaped cover body 140, and a curled elastic member 160 that is arranged inside bag-shaped cover body 140 on an outer side of air bag 150 in the state where the cuff is applied. Bag-shaped cover body 140, air bag 150 and curled elastic member 160 extend with their longitudinal direction corresponding to the winding direction of cuff 130 for the blood pressure monitor. Specifically, in a state where cuff 130 for the blood pressure monitor is applied to a wrist as a measurement site, a width direction of bag-shaped cover body 140 orthogonal to its longitudinal direction is arranged substantially parallel to an axial direction of the wrist (i.e., a direction in which an artery extends).

Bag-shaped cover body 140 has an inner cover member 141 constituting an inner wall portion located on a living body side when applied, and an outer cover member 142 constituting an outer wall portion located on a side opposite to the living body side when applied. Inner cover member 141 and outer cover member 142 are stacked one on the other and their rims are connected to form a bag shape. Inner cover member 141 of bag-shaped cover body 140 is preferably formed of a member with excellent elasticity, and outer cover member 142 of bag-shaped cover body 140 is preferably formed of a member with poor elasticity.

On one end in the longitudinal direction of bag-shaped cover body 140, a loop fastener 165 is provided on the inner peripheral surface. On the other end in the longitudinal direction of bag-shaped cover body 140, a hook fastener 166 is attached to the outer peripheral surface, for engagement with loop fastener 165. Loop and hook fasteners 165 and 166 are members for securing blood pressure monitor 100A on the wrist in a stable manner when cuff 130 is applied to the wrist. At an end portion of outer cover member 142 on which loop fastener 165 is not attached, its tip end is folded inward to form a folded portion 142a, and one end of inner cover member 141 is sandwiched between folded portion 142a and outer cover member 142 adjacent to folded portion 142a.

Air bag 150 is made of a member of a bag shape that is formed using resin sheets. Specifically, air bag 150 is formed into a bag shape by stacking an inner resin sheet 151 located on the wrist side and an outer resin sheet 152 located on a side opposite to the wrist side when cuff 130 for the blood pressure monitor is wound on the wrist one on the other and melting and bonding their rims, and has an inflated/deflated space 154 therein. Inflated/deflated space 154 is connected via a tube 120 to an air system component 121 for blood pressure measurement in main body 110, which will be described later (see FIG. 3).

As the material for inner resin sheet 151 and outer resin sheet 152 constituting air bag 150, any material can be used as long as it exhibits excellent elasticity and prevents leakage of the air from inflated/deflated space 154 after melting and bonding. From these standpoints, optimal materials for inner resin sheet 151 and outer resin sheet 152 include copolymer of ethylene-vinyl acetate (EVA), soft polyvinyl chloride (PVC), polyurethane (PU), crude rubber, and the like.

On the outer side of air bag 150, curled elastic member 160 identified as an elastic member (a curved elastic plate) is arranged, which is wound in an annular shape and elastically deformable in a radial direction. Curled elastic member 160 adheres to the outer peripheral surface of air bag 150 using an adhesive member such as a double-faced tape (not shown). Curled elastic member 160 is configured to maintain its own annular shape corresponding to the contour of the wrist, and facilitates application of cuff 130 on the wrist by the subject himself/herself. Curled elastic member 160 is made of a resin member of polypropylene or the like, so as to exert sufficient elastic force.

Figure 3:
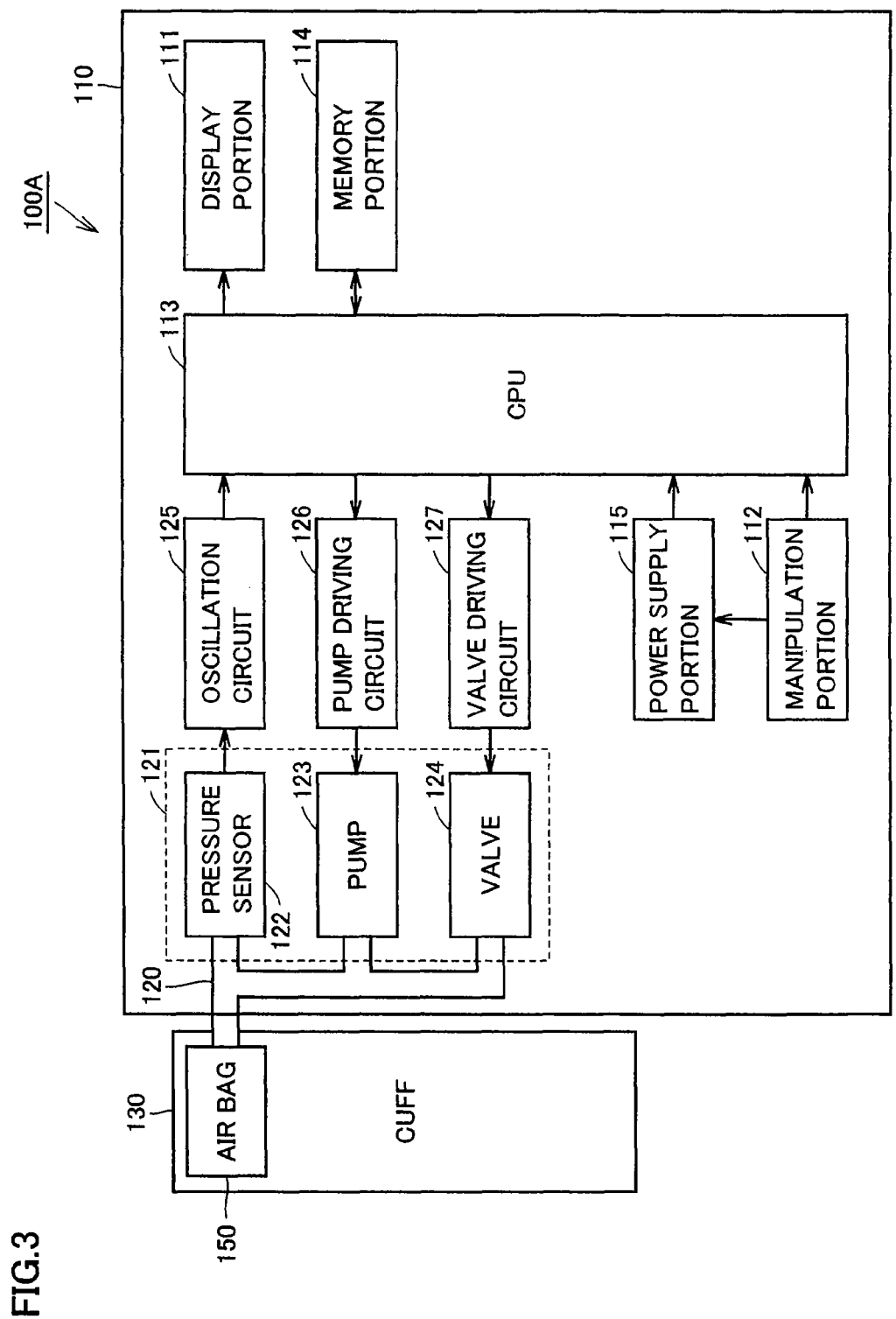
FIG. 3 is a block diagram showing a configuration of the blood pressure monitor according to the embodiment of the present invention.

FIG. 3 is a block diagram showing a configuration of the blood pressure monitor according to the present embodiment. As shown in FIG. 3, main body 110 includes air system component 121 for blood pressure measurement for supplying or evacuating the air to or from the above-described air bag 150 via tube 120, and an oscillation circuit 125, a pump driving circuit 126 and a valve driving circuit 127 which are provided in association with air system component 121 for blood pressure measurement. These components function as an inflating/deflating mechanism for inflating and deflating air 20, bag 150.

Main body 110 further includes a CPU (Central Processing Unit) 113 for controlling and monitoring the respective portions in a centralized manner, a memory portion 114 for storing a program for causing CPU 113 to conduct a prescribed operation and various information including blood pressure values measured, a display portion 111 for displaying various information including a blood pressure measurement result, a manipulation portion 112 manipulated for inputting various instructions for measurement, and a power supply portion 115 for supplying electric power to CPU 113 by an instruction of power ON from manipulation portion 112. CPU 113 also serves as a blood pressure value calculating portion for calculating a blood pressure value.

Air system component 121 for blood pressure measurement has a pressure sensor 122 having an output value changed in accordance with the pressure within air bag 150 (hereinafter, referred to as "cuff pressure"), a pump 123 for supplying the air to air bag 150, and a valve 124 that is opened or closed to introduce or evacuate the air to or from air bag 150. Pressure sensor 122 serves as a pressure detecting portion for detecting the cuff pressure. Oscillation circuit 125 outputs to CPU 113 a signal of oscillation frequency corresponding to the output value of pressure sensor 122. Pump driving circuit 126 controls driving of pump 123 based on a control signal supplied from CPU 113. Valve driving circuit 127 controls opening/closing of valve 124 based on a control signal supplied from CPU 113.

Figure 4:
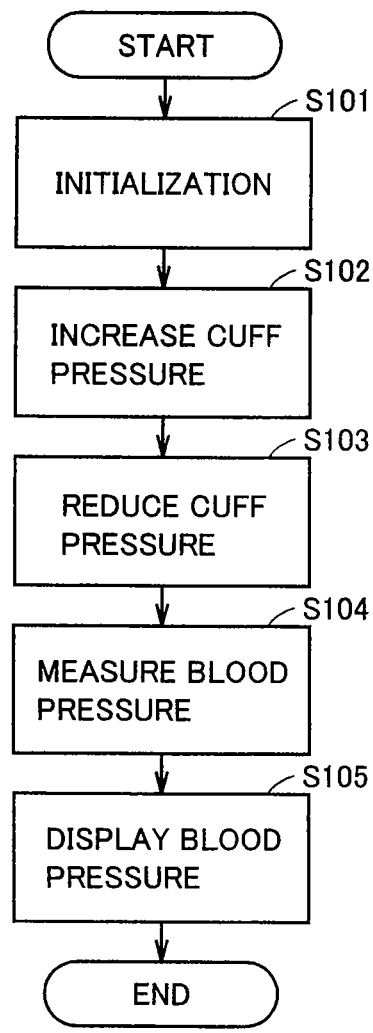
FIG. 4 is a flowchart illustrating a process flow of blood pressure measurement with the blood pressure monitor according to the embodiment of the present invention.

FIG. 4 is a flowchart illustrating a process flow of blood pressure measurement with the blood pressure monitor according to the present embodiment. The program according to this flowchart is prestored in memory portion 114, and the blood pressure measuring process is carried out as CPU 113 reads out this program from memory portion 114 and executes the same.

As shown in FIG. 4, when a subject manipulates a manipulation button on manipulation portion 112 of blood pressure monitor 100A to turn the power ON, blood pressure monitor 100A is initialized (step S101). When it becomes a measurable state, CPU 113 starts driving of pump 123 to gradually increase the cuff pressure of air bag 150 (step S102). During the process of gradually increasing the pressure, when the cuff pressure reaches a prescribed level for measuring the blood pressure, CPU 113 stops pump 123, and gradually opens the closed valve 124 to gradually evacuate the air from air bag 150, so as to gradually reduce the cuff pressure (step S103). In the present embodiment, the blood pressure is measured during the process of gradually decreasing the cuff pressure.

Next, CPU 113 calculates the blood pressure (systolic blood pressure, diastolic blood pressure) in a known manner (step S104). Specifically, during the process where the cuff pressure is gradually decreased, CPU 113 extracts pulse wave information based on the oscillation frequency obtained from oscillation circuit 125. It then calculates the blood pressure value from the pulse wave information extracted. The blood pressure value obtained in step S104 is displayed on display portion 111 (step S105). Although the measurement method described above is based on a so-called "decreasing-pressure measurement method" where the pulse waves are detected while the air bag is being decreased in pressure, it is of course possible to employ a so-called "increasing-pressure measurement method" where the pulse waves are detected while the air bag is being increased in pressure.

Figure 5:
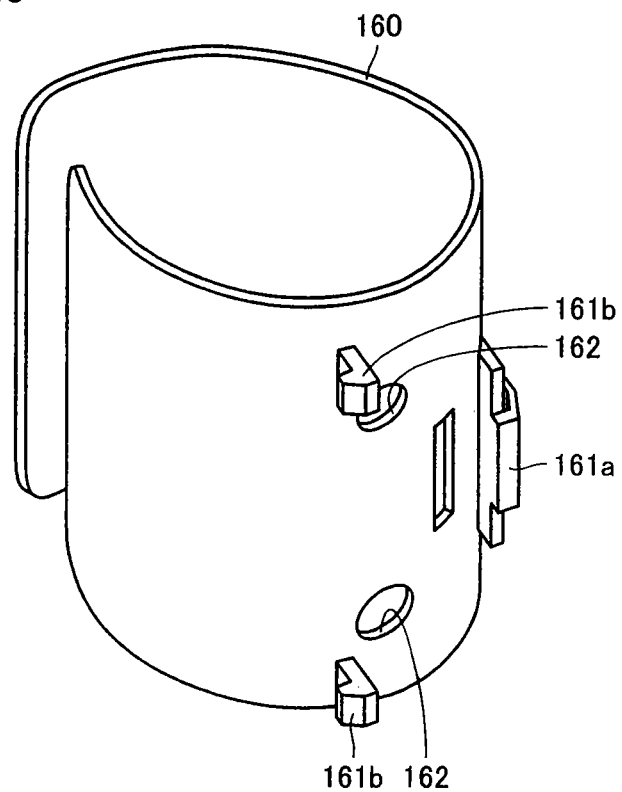
FIG. 5 is a perspective view showing a shape of a curled elastic member of a cuff for a blood pressure monitor according to the embodiment of the present invention.
Figure 6:
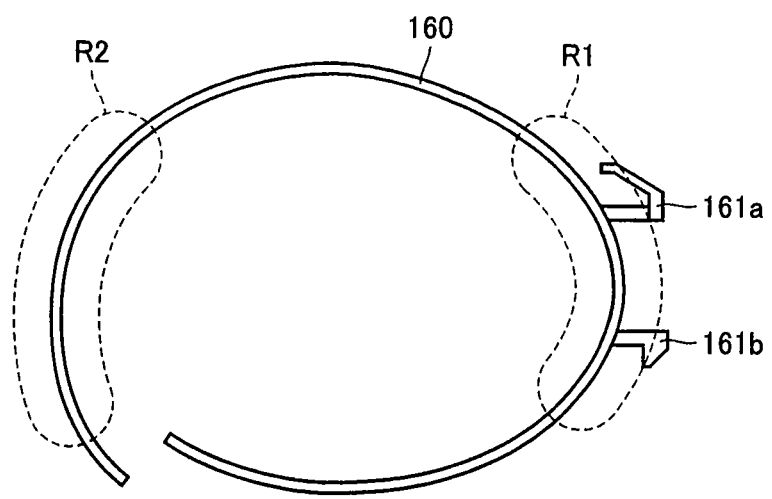
FIG. 6 is a plan view showing the shape of the curled elastic member of the cuff for a blood pressure monitor according to the embodiment of the present invention.

In cuff 130 for the blood pressure monitor of the present embodiment, curled elastic member 160 is designed to have a shape to cause cuff 130 for the blood pressure monitor to fit the wrist with no space therebetween when applied. FIGS. 5 and 6 are views for illustrating a shape of the curled elastic member of the cuff for the blood pressure monitor of the present embodiment, in which FIG. 5 is a perspective view of the curled elastic member and FIG. 6 is a plan view of the curled elastic member. Hereinafter, with reference to these drawings, a specific shape of curled elastic member 160 will be described.

As shown in FIGS. 5 and 6, curled elastic member 160 is formed of a plate-like member having a curved shape, and when it is applied to the wrist, the wrist is inserted into a hollow portion formed therein via a slit provided at a prescribed position in a circumferential direction of curled elastic member 160. Curled elastic member 160 is formed for example by injection molding using a resin material, and engagement hook portions 161a and 161b for securing curled elastic member 160 to main body 110 are provided at prescribed positions on an outer peripheral surface thereof. Further, a hole 162 through which tube 120 described above is inserted is additionally provided at a prescribed position in the outer peripheral surface of curled elastic member 160.

As shown in FIG. 6, curled elastic member 160 has regions with a curvature larger than that of another region (i.e., regions indicated by R1 and R2 in FIG. 6) in a winding direction thereof to fit the wrist with a flattened shape. In cuff 130 for the blood pressure monitor of the present embodiment, the region of curled elastic member 160 indicated by R1 in FIG. 6 represents a region placed along a side portion of the wrist on the radius side when it is applied to the wrist, and the region of curled elastic member 160 indicated by R2 in FIG. 6 represents a region placed along a side portion of the wrist on the ulna side when it is applied to the wrist.

Figure 7:
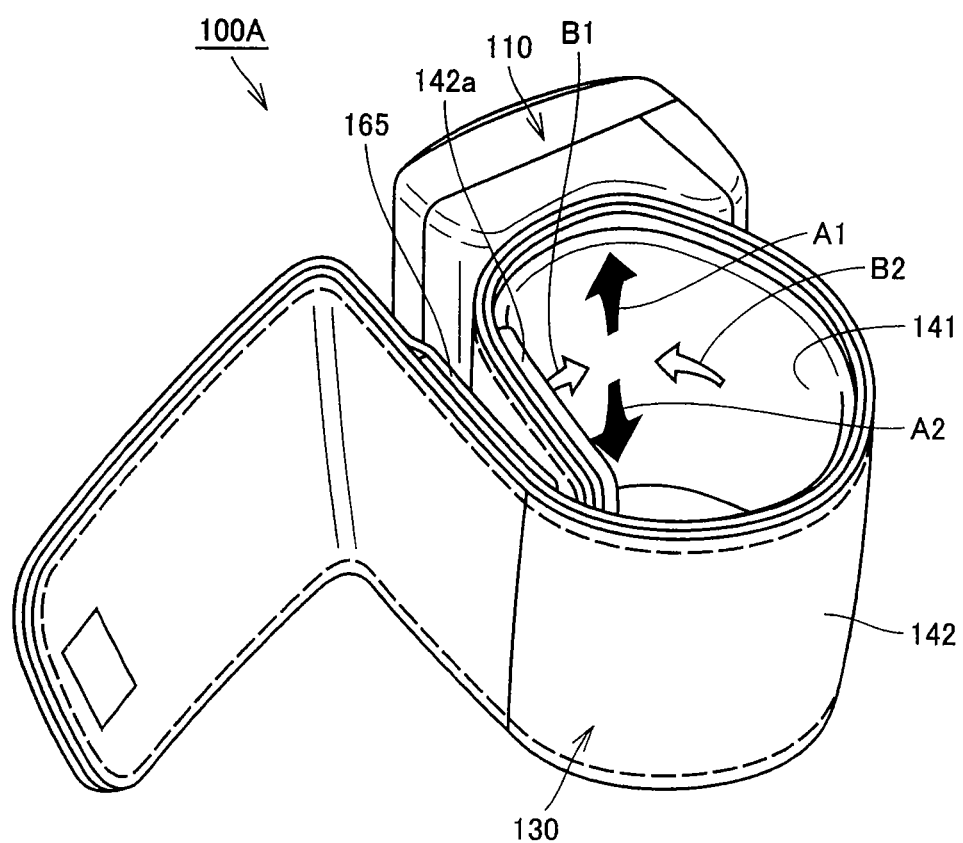
FIG. 7 is a schematic appearance view showing a state where an inner cover member of the cuff for a blood pressure monitor according to the embodiment of the present invention is stretched.
Figure 8B:
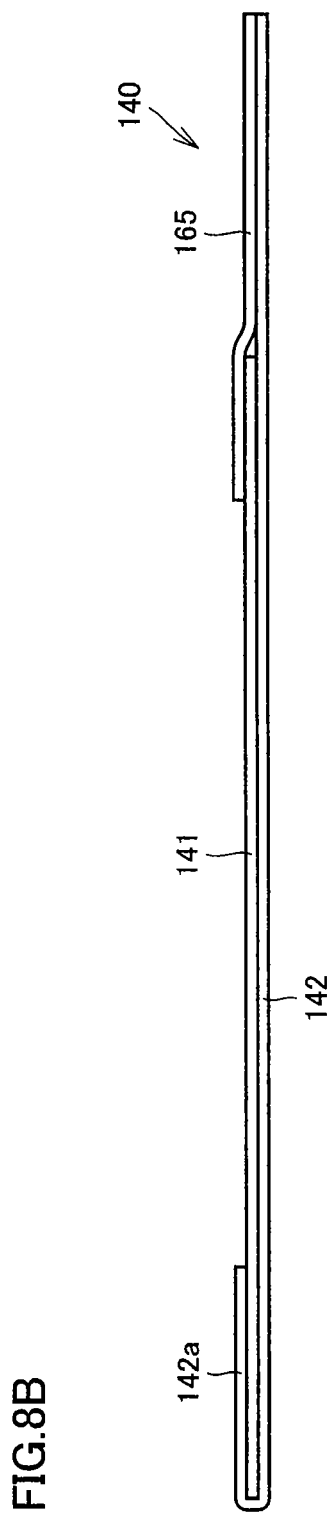
FIG. 8B is a view showing the state where the inner cover member of the cuff for a blood pressure monitor according to the embodiment of the present invention is stretched, which is a schematic side view of the cuff for a the blood pressure monitor when it is developed and seen from the surface to be applied to the living body.

In cuff 130 for the blood pressure monitor of the present embodiment and blood pressure monitor 100A having the same, inner cover member 141 constituting the inner wall portion of bag-shaped cover body 140 is formed to be stretched to conform to the shape of curled elastic member 160 described above. FIGS. 7 and 8A are views showing a state where the inner cover member of the cuff for the blood pressure monitor of the present embodiment is stretched, in which FIG. 7 is an appearance view of the blood pressure monitor seen from an oblique direction, and FIG. 8A is a schematic development view of the cuff for the blood pressure monitor when it is developed and seen from a surface to be applied to the living body. Further, FIG. 8B is a schematic side view of the cuff for the blood pressure monitor when it is developed. Hereinafter, with reference to these drawings, the state where inner cover member 141 of bag-shaped cover body 140 is stretched will be described.

As shown in FIGS. 7, 8A, and 8B, when air bag 150 is deflated (i.e., when no measurement is performed) in cuff 130 for the blood pressure monitor of the present embodiment and blood pressure monitor 100A having the same, portions of inner cover member 141 with excellent elasticity constituting the inner wall portion of bag-shaped cover body 140 that correspond to large curvature regions R1 and R2 of curled elastic member 160 are stretched in the width direction of bag-shaped cover body 140 (i.e., the direction indicated by an arrow X in FIG. 8A). Specifically, as shown in FIGS. 7 and 8A, in the portion corresponding to region R1 of curled elastic member 160, tension is applied to inner cover member 141 in directions indicated by arrows A1 and A2, outwardly in the width direction, and in the portion corresponding to region R2 of curled elastic member 160, tension is applied to inner cover member 141 in directions indicated by arrows A3 and A4, outwardly in the width direction.

On the other hand, inner cover member 141 at a portion corresponding to a small curvature region of curled elastic member 160 (i.e., a region indicated by S in FIG. 8A) is slackened in the width direction, or stretched in the width direction as with inner cover member 141 at the portions corresponding to large curvature regions R1 and R2 of curled elastic member 160. This is because inner cover member 141 at the portion corresponding to small curvature region S of curled elastic member 160 is inherently less likely to have wrinkles, when compared to inner cover member 141 at the portions corresponding to large curvature regions R1 and R2 of curled elastic member 160. Another reason is that, if inner cover member 141 is stretched over an entire area of cuff 130 for the blood pressure monitor, inflation of air bag 150 at the time of measurement may be obstructed.

At a central portion in the width direction of inner cover member 141 at the portion corresponding to small curvature region S of curled elastic member 160, tension is exerted in a longitudinal direction of inner cover member 141, that is, in directions indicated by arrows B1, B2, B3, and B4 in the drawings. This tension is caused in accordance with a general property of a material such as cloth that the material tends to shrink in a direction orthogonal to a stretching direction in which tension is applied.

With the configuration as described above, a slack enough to cause occurrence of wrinkles is not formed in inner cover member 141 of bag-shaped cover body 140 at the portions corresponding to large curvature regions R1 and R2 of curled elastic member 160. Therefore, occurrence of wrinkles in these portions is prevented, and compressive force uniform over the entire area is exerted to the artery when air bag 150 is inflated (i.e., when measurement is being performed). Further, since inner cover member 141 of bag-shaped cover body 140 at the portion corresponding to small curvature region S of curled elastic member 160 is stretched in the longitudinal direction orthogonal to the width direction described above, occurrence of wrinkles in this portion is simultaneously prevented. Therefore, compressive force more uniform over the entire area is exerted to the artery when air bag 150 is inflated. Consequently, a blood pressure value can be measured with high accuracy by providing blood pressure monitor 100A including such cuff 130 for the blood pressure monitor.

Actual fabrication of cuff 130 for the blood pressure monitor with the above configuration can be performed by appropriately adjusting the size in the width direction of a space formed within bag-shaped cover body 140 and the size in the width direction of curled elastic member 160 contained in bag-shaped cover body 140, and making the relative relationship between the size in the width direction of the space described above and the size in the width direction of curled elastic member 160 nonuniform in a longitudinal direction of cuff 130 for the blood pressure monitor. Various methods can be considered as a specific method of fabricating cuff 130. Hereinafter, several of the various methods of fabricating the cuff for the blood pressure monitor with the above configuration will be illustrated as examples and described in detail.

Example 1

Figure 9:
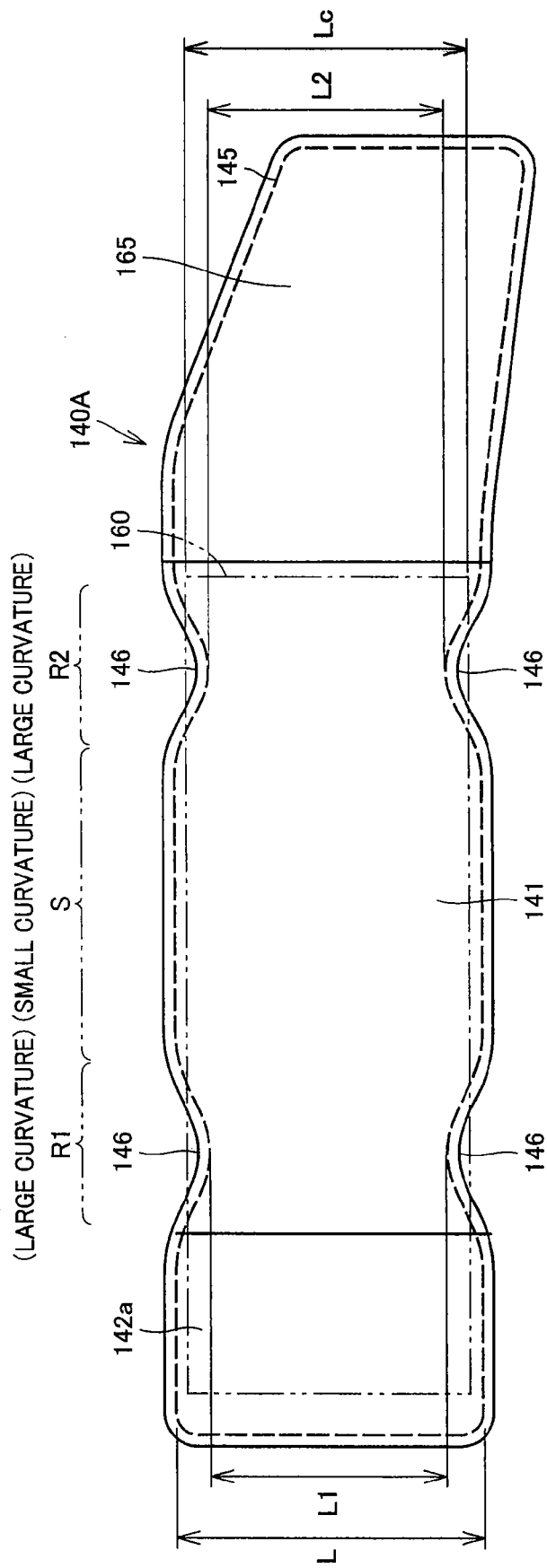
FIG. 9 is a view showing a shape of a bag-shaped cover body of a cuff for a blood pressure monitor in accordance with Example 1, which is a plan view of the bag-shaped cover body after being sewn when seen from a surface to be applied to a living body.

FIG. 9 is a view showing a shape of a bag-shaped cover body of a cuff for a blood pressure monitor in accordance with Example 1, which is a plan view of the bag-shaped cover body after being sewn when seen from a surface to be applied to a living body. In a bag-shaped cover body 140A of the cuff for a blood pressure monitor in accordance with the present example, inner cover member 141 and outer cover member 142 are connected by sewing. It is to be noted that FIG. 9 shows a state before air bag 150 and curled elastic member 160 are inserted into bag-shaped cover body 140A.

As shown in FIG. 9, in bag-shaped cover body 140A in accordance with the present example, a sewn portion 145 is formed at a position a prescribed distance inward of an edge of bag-shaped cover body 140A formed by stacking inner cover member 141 and outer cover member 142 one on the other, and thereby bag-shaped cover body 140A is formed into a bag shape.

In bag-shaped cover body 140A in accordance with the present example, sewing intervals L1 and L2 in the width direction with which inner cover member 141 and outer cover member 142 are sewn at the portions corresponding to large curvature regions R1 and R2 of curled elastic member 160, respectively, are formed smaller than a sewing interval L in the width direction with which inner cover member 141 and outer cover member 142 are sewn at the portion corresponding to small curvature region S of curled elastic member 160. Further, in the state before air bag 150 and curled elastic member 160 are inserted into bag-shaped cover body 140A, sewing intervals L1 and L2 in the width direction with which inner cover member 141 and outer cover member 142 are sewn at the portions corresponding to large curvature regions R1 and R2 of curled elastic member 160, respectively, are formed smaller than a width Lc of the curled elastic member. Here, in bag-shaped cover body 140A in accordance with the present example, the edge of bag-shaped cover body 140A at the portions corresponding to large curvature regions R1 and R2 of curled elastic member 160 is recessed inward to form recessed portions 146, in order to make sewing intervals L1 and L2 in the width direction with which inner cover member 141 and outer cover member 142 are sewn at the portions corresponding to large curvature regions R1 and R2 of curled elastic member 160, respectively, smaller than those at other portions.

With this configuration, as air bag 150 and curled elastic member 160 are inserted into bag-shaped cover body 140A, inner cover member 141 at the portions corresponding to large curvature regions R1 and R2 of curled elastic member 160 can be placed in a state stretched in the width direction. Consequently, cuff 130 for a blood pressure monitor including inner cover member 141 in the stretched state described in the above embodiment can be fabricated extremely easily.

Example 2

Figure 10:
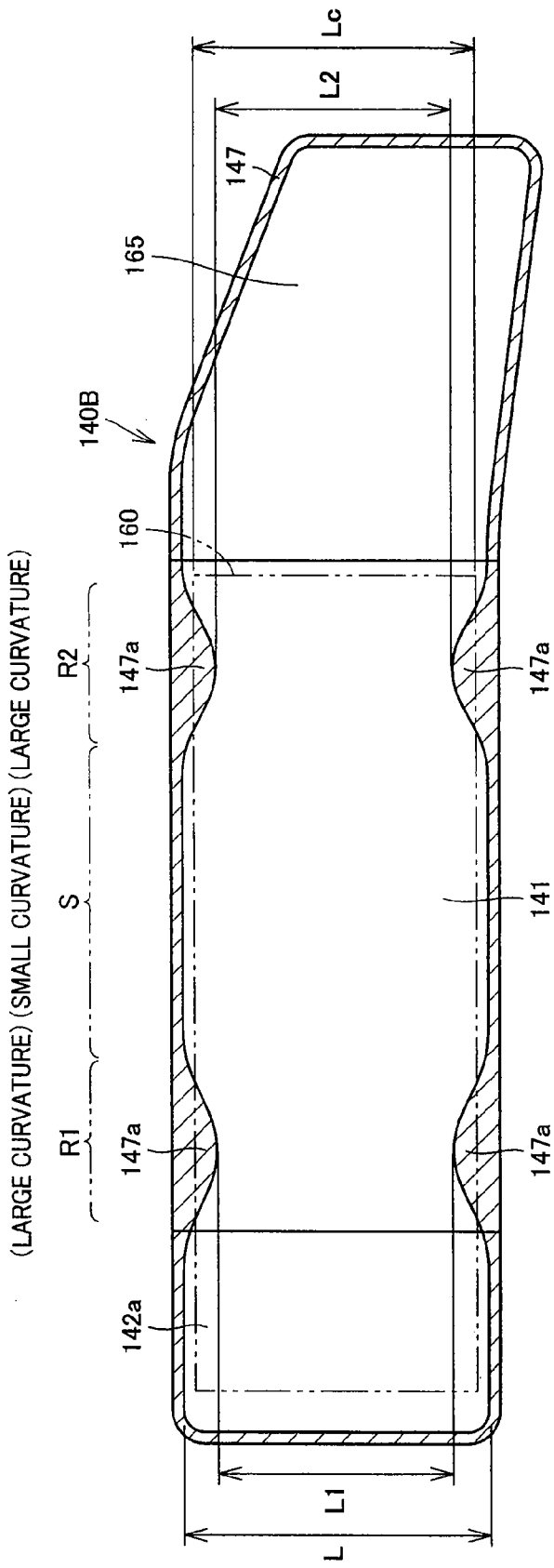
FIG. 10 is a view showing a shape of a bag-shaped cover body of a cuff for a blood pressure monitor in accordance with Example 2, which is a plan view of the bag-shaped cover body after being melted and bonded when seen from a surface to be applied to a living body.

FIG. 10 is a view showing a shape of a bag-shaped cover body of a cuff for a blood pressure monitor in accordance with Example 2, which is a plan view of the bag-shaped cover body after being melted and bonded when seen from a surface to be applied to a living body. In a bag-shaped cover body 140B of the cuff for a blood pressure monitor in accordance with the present example, inner cover member 141 and outer cover member 142 are connected by melting and bonding. FIG. 10 shows a state before air bag 150 and curled elastic member 160 are inserted into bag-shaped cover body 140B.

As shown in FIG. 10, in bag-shaped cover body 140B in accordance with the present example, a bonded portion 147 is formed to have a melting and bonding allowance of a prescribed distance from an edge of bag-shaped cover body 140B formed by stacking inner cover member 141 and outer cover member 142 one on the other, and thereby bag-shaped cover body 140B is formed into a bag shape.

In bag-shaped cover body 140B in accordance with the present example, melting and bonding intervals L1 and L2 in the width direction with which inner cover member 141 and outer cover member 142 are melted and bonded at the portions corresponding to large curvature regions R1 and R2 of curled elastic member 160, respectively, are formed smaller than a melting and bonding interval L in the width direction with which inner cover member 141 and outer cover member 142 are melted and bonded at the portion corresponding to small curvature region S of curled elastic member 160. Further, in the state before air bag 150 and curled elastic member 160 are inserted into bag-shaped cover body 140B, melting and bonding intervals L1 and L2 in the width direction with which inner cover member 141 and outer cover member 142 are melted and bonded at the portions corresponding to large curvature regions R1 and R2 of curled elastic member 160, respectively, are formed smaller than width Lc of the curled elastic member. Here, in bag-shaped cover body 140B in accordance with the present example, the melting and bonding allowance from the edge of bag-shaped cover body 140B at the portions corresponding to large curvature regions R1 and R2 of curled elastic member 160 is wider at portions indicated by 147a than the melting and bonding allowance at other portions of bonded portion 147, in order to make the melting and bonding intervals in the width direction with which inner cover member 141 and outer cover member 142 are melted and bonded at the portions corresponding to large curvature regions R1 and R2 of curled elastic member 160, respectively, smaller than those at other portions.

With this configuration, as with Example 1 described above, as air bag 150 and curled elastic member 160 are inserted into bag-shaped cover body 140B, inner cover member 141 at the portions corresponding to large curvature regions R1 and R2 of curled elastic member 160 can be placed in a state stretched in the width direction. Consequently, cuff 130 for a blood pressure monitor including inner cover member 141 in the stretched state described in the above embodiment can be fabricated extremely easily.

Example 3

Figure 11:
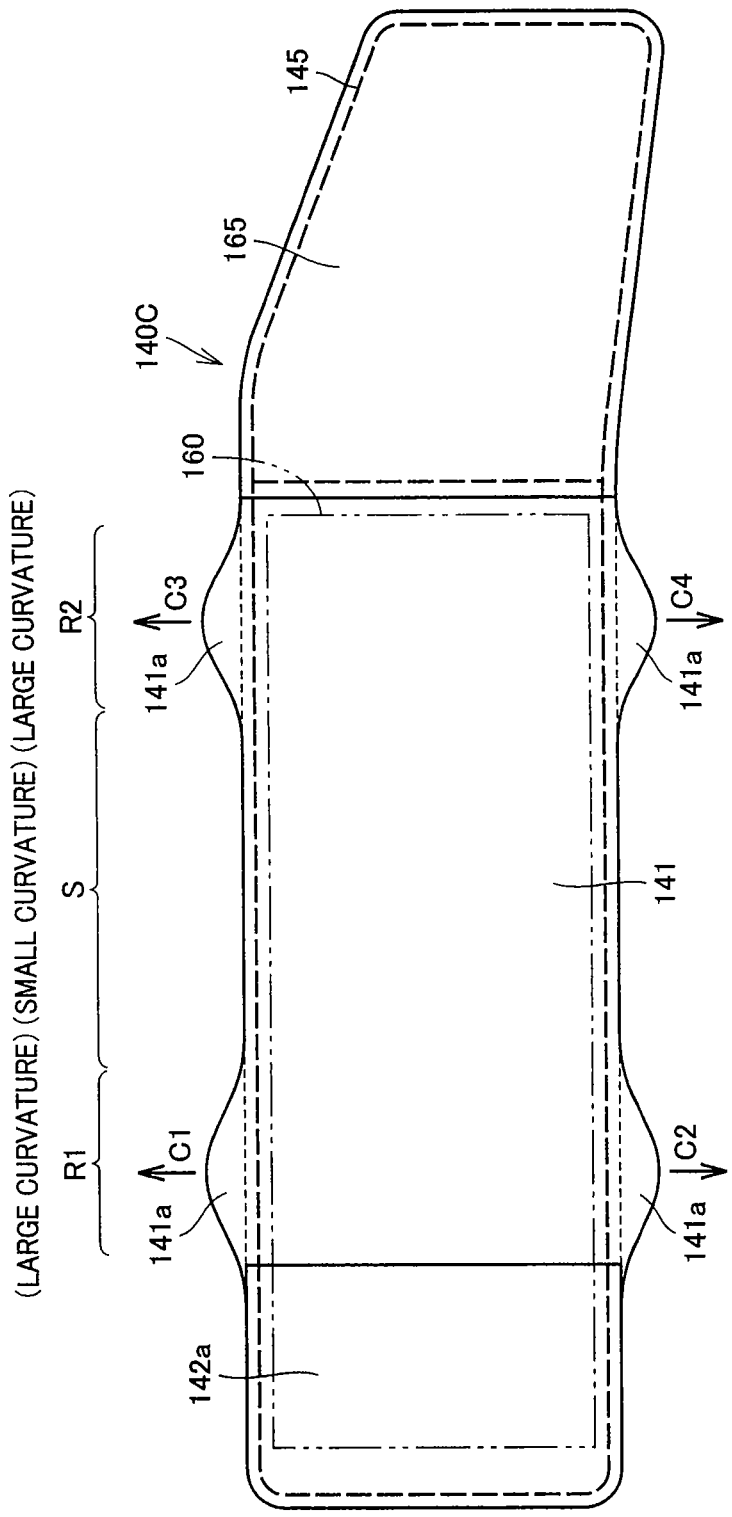
FIG. 11 is a view of a bag-shaped cover body of a cuff for a blood pressure monitor in accordance with Example 3 at the time of sewing, which is a plan view of the bag-shaped cover body when seen from a surface to be applied to a living body.

FIG. 11 is a view showing a shape of a bag-shaped cover body of a cuff for a blood pressure monitor in accordance with Example 3, which is a plan view of the bag-shaped cover body at the time of sewing when seen from a surface to be applied to a living body. In a bag-shaped cover body 140C of the cuff for a blood pressure monitor in accordance with the present example, inner cover member 141 and outer cover member 142 are connected by sewing. FIG. 11 shows a state before air bag 150 and curled elastic member 160 are inserted into bag-shaped cover body 140C.

As shown in FIG. 11, in bag-shaped cover body 140C in accordance with the present example, portions 141a of inner cover member 141 corresponding to large curvature regions R1 and R2 of curled elastic member 160 are placed in a state stretched toward directions indicated by arrow C1, C2, C3, and C4, respectively, and inner cover member 141 is sewn to outer cover member 142 with this state maintained.

With this configuration, inner cover member 141 at the portions corresponding to large curvature regions R1 and R2 of curled elastic member 160 can be placed in a state stretched in the width direction. Consequently, cuff 130 for a blood pressure monitor including inner cover member 141 in the stretched state described in the above embodiment can be fabricated extremely easily. It is to be noted that, in the cuff for a blood pressure monitor in accordance with the present example, inner cover member 141 at the portions corresponding to large curvature regions R1 and R2 of curled elastic member 160 can be placed in a state stretched in the width direction, irrespective of whether curled elastic member 160 is inserted.

Example 4

Figure 12:
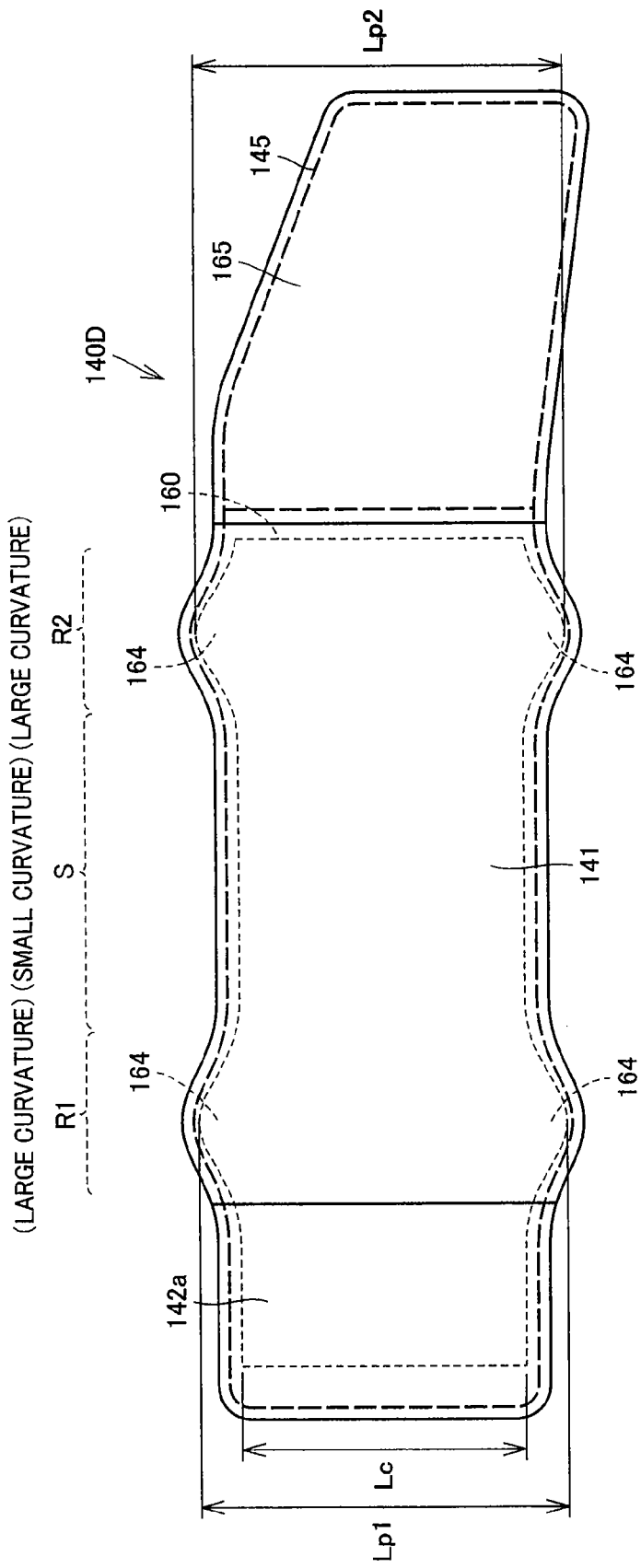
FIG. 12 is a view showing a configuration of a cuff for a blood pressure monitor in accordance with Example 4, which is a schematic development view of the cuff for a blood pressure monitor when it is developed and seen from a surface to be applied to a living body.
Figure 13:
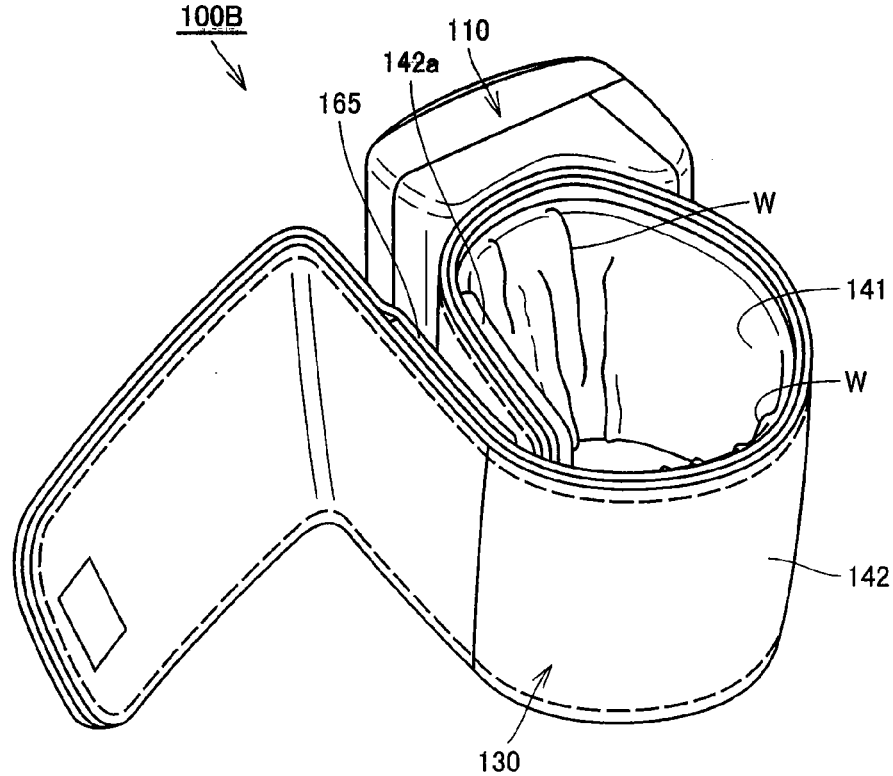
FIG. 13 is a perspective view of a conventional ordinary wrist blood pressure monitor.
Figure 14:
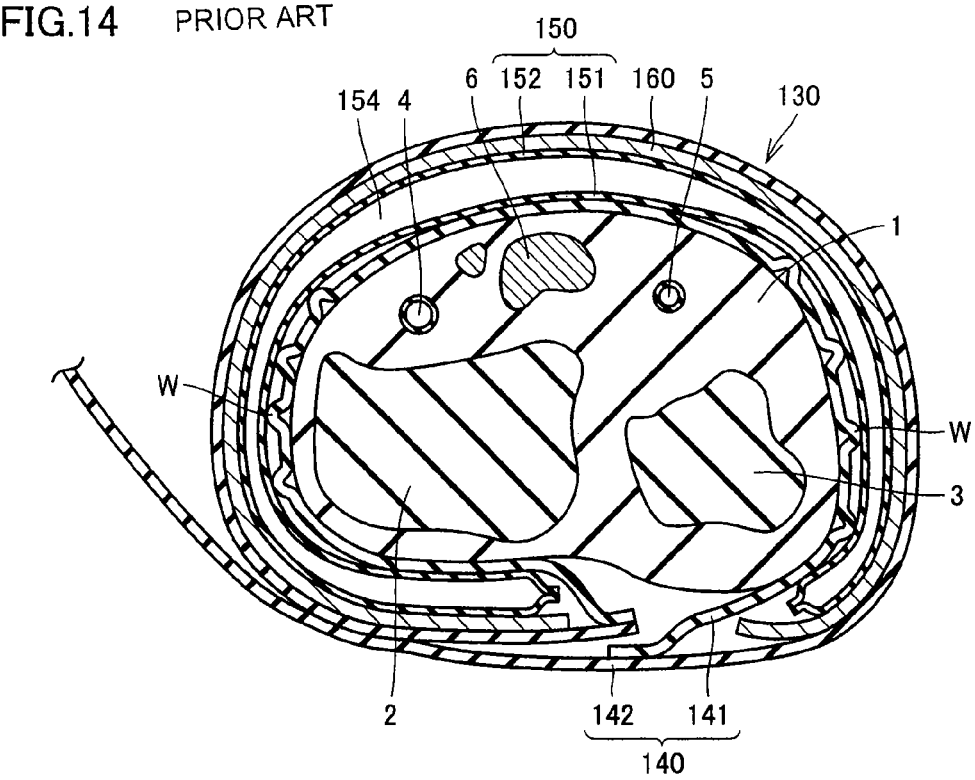
FIG. 14 is a cross sectional view showing a state where a cuff for the wrist blood pressure monitor shown in FIG. 13 is wound on a wrist.

FIG. 12 is a view showing a configuration of a cuff for a blood pressure monitor in accordance with Example 4, which is a schematic development view of the cuff for a blood pressure monitor when it is developed and seen from a surface to be applied to a living body. In a bag-shaped cover body 140D of the cuff for a blood pressure monitor in accordance with the present example, inner cover member 141 and outer cover member 142 are connected by sewing. FIG. 12 shows a state after air bag 150 and curled elastic member 160 are inserted into bag-shaped cover body 140D.

As shown in FIG. 12, in bag-shaped cover body 140D in accordance with the present example, projecting portions 164 are formed to project from an edge in the width direction at large curvature regions R1 and R2 of curled elastic member 160 outwardly in the width direction, and thereby widths Lp1 and Lp2 of curled elastic member 160 at large curvature regions R1 and R2 of curled elastic member 160, respectively, are formed greater than width Lc of curled elastic member 160 at small curvature region S of curled elastic member 160. Further, in the state before air bag 150 and curled elastic member 160 are inserted into bag-shaped cover body 140D, the sewing intervals in the width direction with which inner cover member 141 and outer cover member 142 are sewn at the portions corresponding to large curvature regions R1 and R2 of curled elastic member 160, respectively, are formed smaller than widths Lp1 and Lp2 of curled elastic member 160 at large curvature regions R1 and R2 of curled elastic member 160, respectively.

With this configuration, as with Example 1 described above, as air bag 150 and curled elastic member 160 are inserted into bag-shaped cover body 140D, inner cover member 141 at the portions corresponding to large curvature regions R1 and R2 of curled elastic member 160 can be placed in a state stretched in the width direction. Consequently, cuff 130 for a blood pressure monitor including inner cover member 141 in the stretched state described in the above embodiment can be fabricated extremely easily.

In the cuff for a blood pressure monitor of the present embodiment described above, the description has been given of the case where the inner cover member is formed of cloth with elasticity higher than that of the outer cover member. The present invention is not particularly limited to such a configuration, and for example, the inner cover member and the outer cover member may be formed of the same type of material. Generally, however, it is preferable to use a material with high elasticity for the inside. As the inner cover member, knitted cloth, nonwoven cloth, foam sheet, or the like can be suitably used, for example. As the outer cover member, a laminated body including polyvinyl chloride (PVC) and woven cloth or the like can be used, for example.

Further, in the cuff for a blood pressure monitor in accordance with the examples described above, the description has been given of the case where the inner cover member and the outer cover member are connected by sewing, or melting and bonding. Both may be performed simultaneously, and the inner cover member and the outer cover member may be connected by a technique other than those, such as adhesion with an adhesive, or using a retaining member such as a clip.

Further, in the embodiment described above, the description has been given of the case where the present invention is applied to a cuff for use in a wrist blood pressure monitor assuming the wrist as the measurement site. However, the present invention is applicable to a cuff for any type of blood pressure monitor, including an upper arm type and a finger type.

The embodiment disclosed herein is by way of example in all respects and should not be interpreted as restrictive. The scope of the present invention is determined by the appended claims, and intended to include all the modifications within the meaning and the scope equivalent to those of the claims.

The invention claimed is:
1. A cuff for a blood pressure monitor, comprising:
a fluid bag inflated and deflated as a fluid comes in and out;
an elastic member located on an outer side of said fluid bag when said fluid bag is wound around an object, and wound annularly and elastically deformable in a radial direction; and
a bag-shaped cover body containing said fluid bag and said elastic member therein and configured to be applied to the object such that a width direction thereof is substan- tially transverse to a direction in which the fluid bag is wound around the object, wherein said bag-shaped cover body includes an inner wall portion located on an object side when the bag-shaped cover body is wound around the object, and an outer wall portion located on a side opposite to the object side when the bag-shaped cover body is wound around the object, said elastic member includes a large curvature region and a small curvature region in a winding direction thereof to cause the cuff for a blood pressure monitor to fit the object, and in a state where said fluid bag is deflated and is not wound around the object, said inner wall portion of said bag-shaped cover body at a portion corresponding to the large curvature region of said elastic member is stretched in said width direction so that a tension is applied in the width direction, and said inner wall portion at a portion corresponding to the small curvature region of said elastic member is slackened in said width direction.

2. The cuff for a blood pressure monitor according to claim 1, wherein, in the state where said fluid bag is deflated and is not wound around the object, said inner wall portion at the portion corresponding to the large curvature region of said elastic member is more stretched in said width direction than said inner wall portion at a portion corresponding to the small curvature region of said elastic member.

3. The cuff for a blood pressure monitor according to claim 1, wherein said inner wall portion is more elastic than said outer wall portion.

4. The cuff for a blood pressure monitor according to claim 1, wherein said bag-shaped cover body is formed into a bag shape by stacking an inner cover member forming said inner wall portion and an outer cover member forming said outer wall portion one on the other and connecting their rims, and in a state after said fluid bag and said elastic member are inserted into said bag-shaped cover body and where said fluid bag is deflated and is not wound around the object, said inner cover member at a portion corresponding to the large curvature region of said elastic member is stretched in said width direction, by forming a connection interval in said width direction with which said inner cover member and said outer cover member are connected at a portion corresponding to the large curvature region of said elastic member to be smaller than a connection interval in said width direction with which said inner cover member and said outer cover member are connected at a portion corresponding to the small curvature region of said elastic member, and, in a state before said fluid bag and said elastic member are inserted into said bag-shaped cover body, forming the connection interval in said width direction with which said inner cover member and said outer cover member are connected at the portion corresponding to the large curvature region of said elastic member to be smaller than a width of said elastic member.

5. The cuff for a blood pressure monitor according to claim 4, wherein said inner cover member and said outer cover member are connected by sewing, and/or melting and bonding.

6. The cuff for a blood pressure monitor according to claim 1, wherein said bag-shaped cover body is formed into a bag shape by stacking an inner cover member forming said inner wall portion and an outer cover member forming said outer wall portion one on the other and connecting their rims, and in the state where said fluid bag is deflated and is not wound around the object, said inner cover member at a portion corresponding to the large curvature region of said elastic member is stretched in said width direction, by placing said inner cover member at the portion corresponding to the large curvature region of said elastic member in a stretched state and connecting said inner cover member to said outer cover member with this state maintained.

7. The cuff for a blood pressure monitor according to claim 6, wherein said inner cover member and said outer cover member are connected by sewing, and/or melting and bonding.

8. The cuff for a blood pressure monitor according to claim 1, wherein said bag-shaped cover body is formed into a bag shape by stacking an inner cover member forming said inner wall portion and an outer cover member forming said outer wall portion one on the other and connecting their rims, and in a state after said fluid bag and said elastic member are inserted into said bag-shaped cover body and where said fluid bag is deflated and is not wound around the object, said inner cover member at a portion corresponding to the large curvature region of said elastic member is stretched in said width direction, by forming a width of said elastic member at the large curvature region of said elastic member to be greater than a width of said elastic member at the small curvature region of said elastic member, and, in a state before said fluid bag and said elastic member are inserted into said bag-shaped cover body, forming a connection interval in said width direction with which said inner cover member and said outer cover member are connected at a portion corresponding to the large curvature region of said elastic member to be smaller than the width of said elastic member at the large curvature region of said elastic member.

9. The cuff for a blood pressure monitor according to claim 8, wherein said inner cover member and said outer cover member are connected by sewing, and/or melting and bonding.

10. A blood pressure monitor, comprising:
the cuff for a blood pressure monitor according to claim 1;
an inflating/deflating mechanism inflating and deflating said fluid bag;
a pressure detecting portion detecting a pressure within said fluid bag; and
a blood pressure value calculating portion calculating a blood pressure value based on pressure information detected by said pressure detecting portion.

11. The cuff for a blood pressure monitor according to claim 1, wherein the stretching in said width direction of said inner wall portion at a portion corresponding to the large curvature region of said elastic member in a state where said fluid bag is deflated is configured to reduce the formation of wrinkles in said bag-shaped cover body.

* * * * *